United States Patent [19]

Harris et al.

[11] Patent Number: 4,658,819
[45] Date of Patent: Apr. 21, 1987

[54] ELECTROSURGICAL GENERATOR

[75] Inventor: Frank W. Harris, Boulder, Colo.; Frederick M. Hulett, Hayward, Calif.

[73] Assignee: Valleylab, Inc., Boulder, Colo.

[21] Appl. No.: 531,758

[22] Filed: Sep. 13, 1983

[51] Int. Cl.$^4$ .............................................. A61B 17/36
[52] U.S. Cl. .............................. 128/303.13; 128/783
[58] Field of Search ................. 128/303.13, 303.14, 128/303.17, 783

[56] References Cited

U.S. PATENT DOCUMENTS

| 3,601,126 | 8/1971 | Estes | 128/783 |
| 3,699,967 | 10/1972 | Anderson | 128/303.14 |
| 3,885,569 | 5/1975 | Judson | 128/303.14 |
| 3,897,788 | 8/1975 | Newton | 128/303.17 |
| 3,933,157 | 1/1976 | Bjurwill et al. | 128/303.14 |
| 3,963,030 | 6/1976 | Newton | 128/303.17 |
| 3,964,487 | 6/1976 | Judson | 128/303.14 |
| 4,092,986 | 6/1978 | Schneiderman | 128/303.17 |
| 4,126,137 | 11/1978 | Archibald | 128/303.14 |
| 4,188,927 | 2/1980 | Harris | 128/303.17 |
| 4,209,018 | 6/1980 | Meinke et al. | 128/303.17 |
| 4,231,372 | 11/1980 | Newton | 128/303.17 |
| 4,416,277 | 11/1983 | Newton et al. | 128/303.13 |

Primary Examiner—Kyle L. Howell
Assistant Examiner—Ruth S. Smith
Attorney, Agent, or Firm—Gerald J. Ferguson, Jr.; Michael P. Hoffman; Ronni S. Malamud

[57] ABSTRACT

An electrosurgical generator having a source of electrosurgical energy connected to a patient and including control circuitry for decreasing the output power from the source with increasing patient impedance, the rate of power decrease being substantially greater than that which would result if the output voltage from the source were maintained constant over the range of increasing patient impedance. The control circuitry may, in particular, decrease the output power over the range of increasing patient impedance in accordance with the square of the impedance.

21 Claims, 5 Drawing Figures

ELECTROSURGICAL GENERATOR

REFERENCE TO RELATED APPLICATION

This application is related to an application, Ser. No. 531,621 filed By Frederic M. Hulett, III, on even date herewith entitled "Microprocessor Implemented Electrosurgical Generator, now abandoned.

BACKGROUND OF INVENTION

This invention relates to electrosurgical generators and in particular to such generators including means for controlling the output power level thereof. The invention further relates to the use of such generators with bipolar forceps or handpieces.

Bipolar electrosurgery refers to the use of a handpiece having two small electrodes to apply electrosurgical current instead of a single small active and a large return electrode as is used in monopolar electrosurgery.

The advantages of bipolar electrosurgery over monopolar are:

(1) A lower power level is used which translates directly to less tissue destruction.
(2) The only tissue destroyed is that located between the bipolar electrodes so that there is virtually no danger of alternate site burns.
(3) The applied voltage can be much lower. This prevents tissue charring and scarring due to sparks at the electrodes.

Bipolar electrosurgery is used extensively in surgical procedures on the eye and brain where the delicate tissue can be easily damaged by excessive heat or sparking.

SUMMARY OF INVENTION

In an effort to improve the effects of bipolar electrosurgery, studies have been conducted on the variation of tissue impedance during desiccation. The results showed two phases of desiccation. The first phase begins as soon as electrosurgical power is applied. The tissue temperature rises, cell walls are ruptured and the impedance of the tissue shows a decrease. The temperature continues to rise and the water is driven off as steam. As the tissue dries out, the resistance rises. The output voltage goes up somewhat as the resistance rises and at this point sparking, excessive heating of the forceps, or sticking of forceps to tissue may occur.

Accordingly, it is a primary object of this invention to provide an improved electrosurgical generator whose power decreases rapidly with increasing impedance so that the power diminishes towards the end of the desiccation phase.

It is a further object of this invention to provide an improved generator of the foregoing type where the power decreases as the inverse of the square of the tissue impedance.

It is a further object of this invention to provide an improved generator of the foregoing type for use in bipolar electrosurgery.

Other objects and advantages of this invention will be apparent from a reading of the following specification and claims taken with the drawing.

DISCUSSION OF PRIOR ART

U.S. Pat. Nos. 3,946,487; 3,980,085; 4,188,927, and 4,092,986 disclose means for reducing the output current in accordance with increasing load impedance. In particular, these patents teach the use of constant voltage outputs whereby the current is decreased with increasing load impedance. However, there is no disclosure in these patents that output power be inversely varied in accordance with the square of the load impedance. In general, there is no disclosure the output power be decreased at a rate which is substantially greater than that which results in the constant voltage outputs of these patents.

DETAILED DESCRIPTION OF PREFERRED EMBODIMENT OF THE INVENTION

Figure 1:
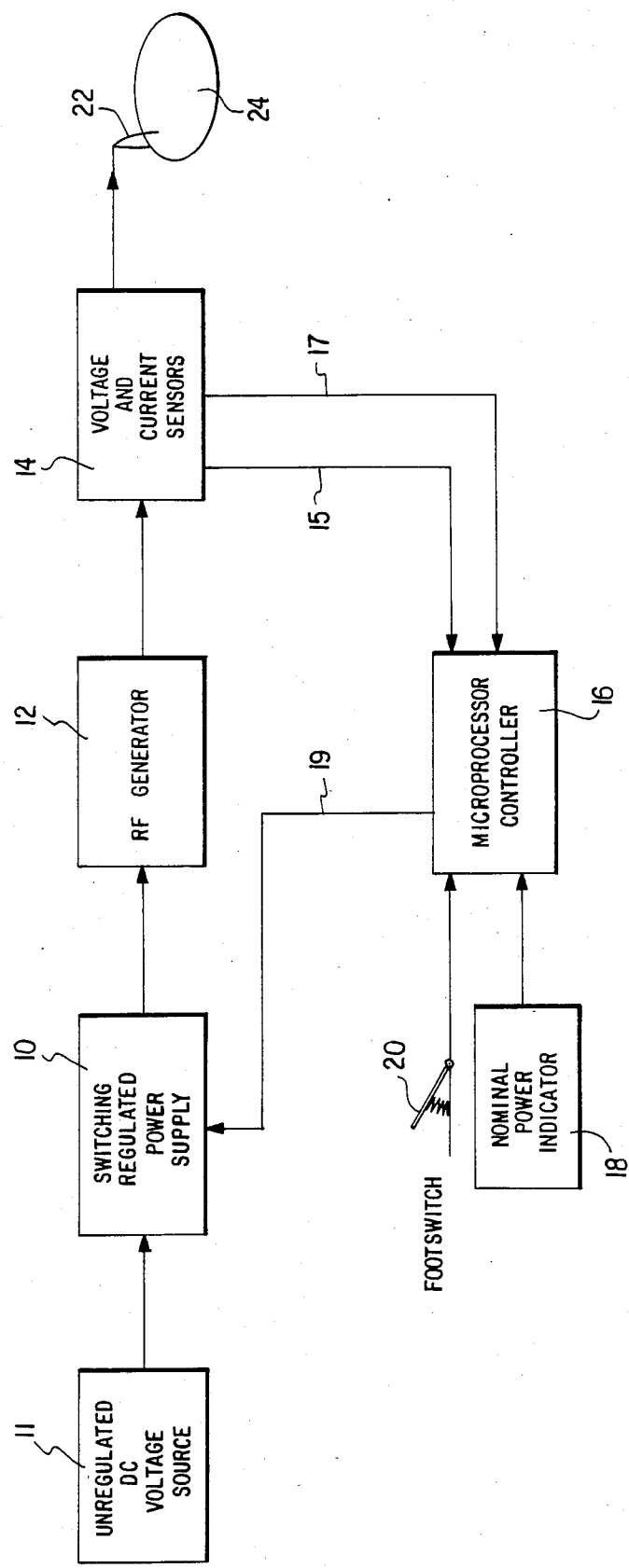
FIG. 1 is a block diagram of an illustrated electrosurgical generator in accordance with the invention.

Reference should be made to the drawing where like reference numerals refer to like parts.

Referring to FIG. 1, an illustrative electrosurgical generator in accordance with the invention includes a switching regulated power supply 10, an unregulated DC voltage source 11, an RF generator 12, voltage and current sensors 14, a microprocessor controller 16, a nominal power indicator 18, and a footswitch 20. Electrosurgical current is applied from the generator to forceps 22, which are diagramatically shown in contact with a patient 24.

The power delivered to the load is a function of the voltage from DC supply 10 and the load impedance. As will be described in more detail hereinafter, sensors 14 develop sensing signals proportional to the load voltage and current which are respectively applied over lines 15 and 17 to controller 16. The controller digitizes the sensing signals and computes the load impedance and the actual power being delivered to the load.

Figure 2:
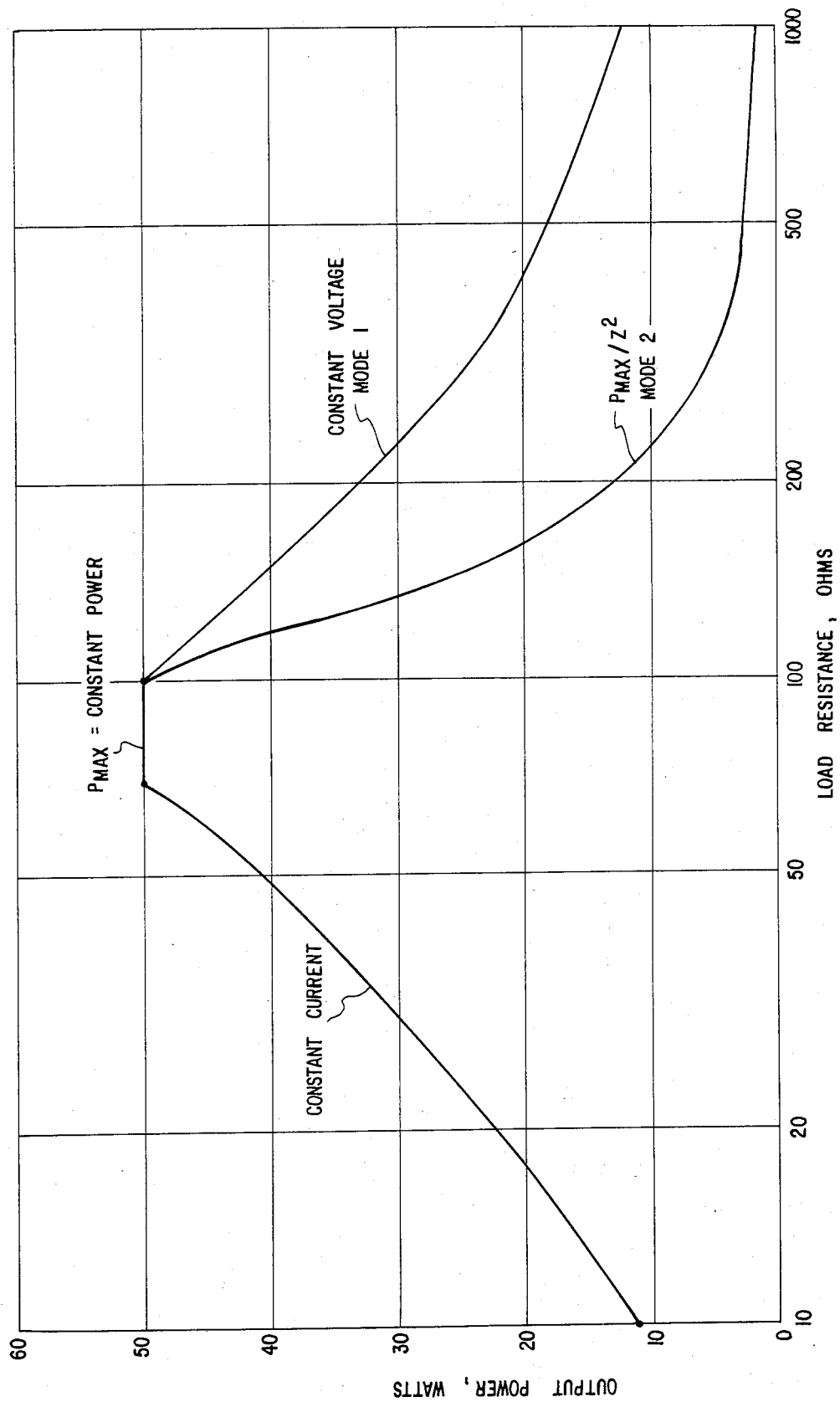
FIG. 2 is a graph illustrating different modes of operation of the generator of the present invention.

A required load power is also calculated which is a function of the calculated load impedance and the nominal power selected by the operator at 18. A graph of the required load power for a nominal power of 50 watts is illustrated in FIG. 2.

At low load impedances less than typically 70 ohms, the computed required power is reduced to prevent damage or overheating of the RF output. In particular, the control voltage applied over line 19 to supply 10 controls the output power in such a manner as to maintain the load current constant over this low value impedance range. Over a mid range extending from about 70 to 100 ohms, the computed required power is held constant at the selected nominal power.

At impedances above 100 ohms, one of two modes may be chosen by the operator. As indicated in FIG. 2, the computed required power is reduced in the first of these modes with the voltage being held constant, this effect being similar to that of known generators. In the second mode the computed required power is reduced at a rate which is substantially greater than that which occurs when the voltage is held constant. Preferably, the computed required power is reduced, in the second mode, as the square of the load impedance. Thus, for example, the computed required power for a load having an impedance of 200 ohms is one-fourth that required for a load impedance of 100 ohms. When the impedance is increased to about 800 ohms, for example, in the second mode of operation, a constant voltage characteristic may be implemented since at this level, the power levels may become impractically small.

After the required power has been calculated for a given nominal power and load impedance range, a comparison is then effectively made between the required power and the actual power to adjust the control voltage applied to line 19 by the correct amount to cause the actual power to match the required power.

The load impedance varies continuously during electrosurgery due to differing amounts of tissue contact, tissue heating, etc. The microprocessor controller 16 accordingly repeats the measurement, calculation and correction process approximately every 20 milliseconds as long as the foot switch 20 or bipolar handswitch (not shown) is closed.

Figure 3:
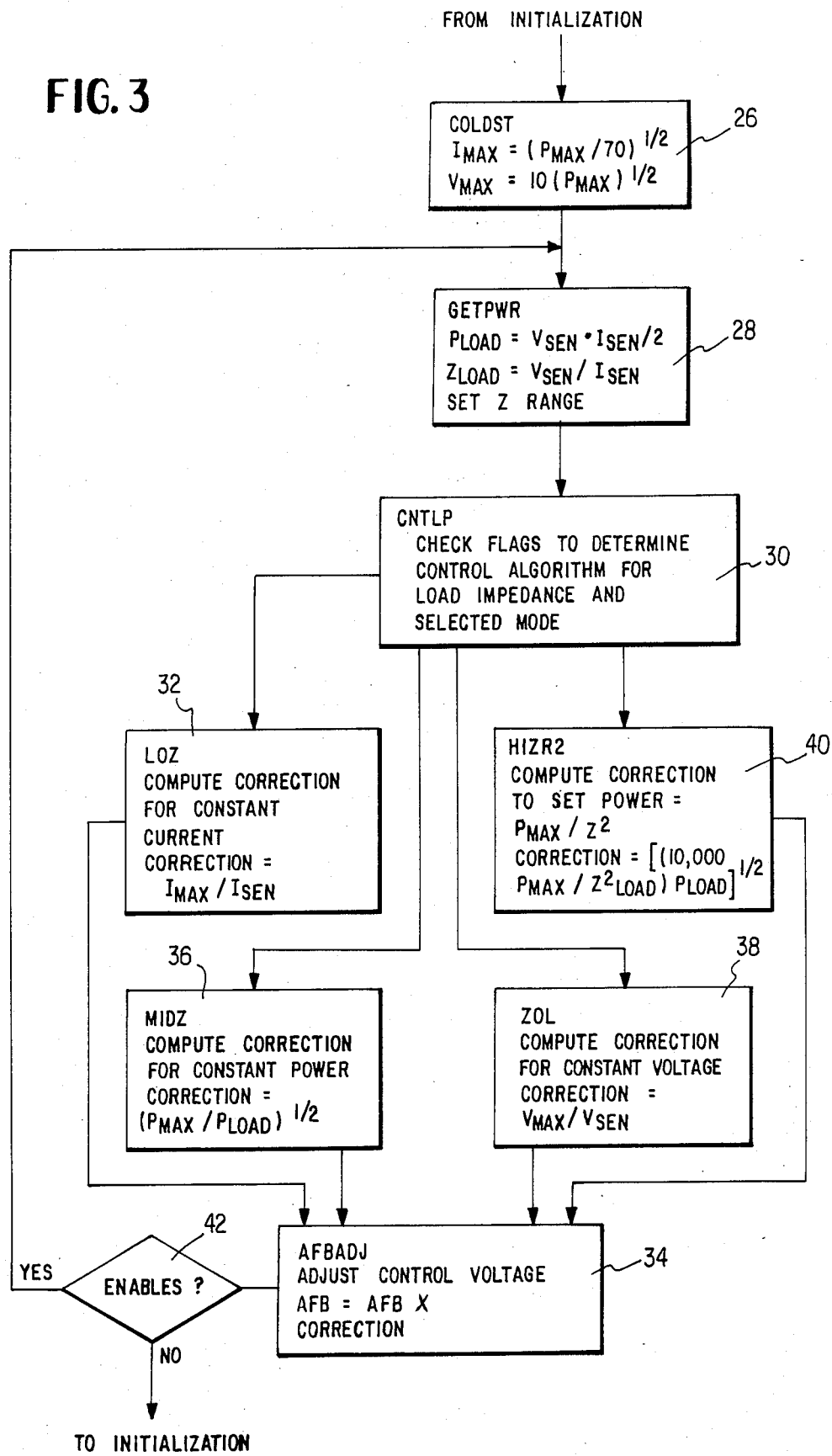
FIG. 3 is a flow chart of the program executed by and stored in the microprocessor controller of FIG. 1.

Reference should now be made to FIG. 3, which is a generalized flow chart of the program executed by microprocessor controller 16 where the microprocessor may be an INTEL 8039, a member of the 8048 family of singlechip microcomputers and where the program may be stored on an INTEL 2716 programmable memory. After certain initialization routines (not shown), program control passes to routine COLDST 26 (COLD START), which calculates certain parameters and initiates certain functions. First it calculates $I_{MAX}$, which is the current value which should occur at 70 ohms for a given nominal power selected by the operator. For example, if the operator selects a nominal power of 70 watts, the current delivered to a 70 ohm load will be 1 ampere and thus $I_{MAX}$ is 1 ampere in this case. The nominal power range available to the operator typically extends from 0 to 70 watts. The nominal power selected by the operator is termed $P_{MAX}$ and occurs over the mid range impedance extending from 70 to 100 ohms. Since the maximum power occurs over the 70 to 100 ohm range, and since the largest current which will occur in this range occurs at 70 ohms, $I_{MAX}$ is calculated at 70 ohms as described above. In general, $I_{MAX}=(P_{MAX}/70)^{\frac{1}{2}}$ where $P_{MAX}$ equals the nominal power selected by the operator and 70 corresponds to a 70 ohm load.

COLDST also calculates the initial parameter $V_{MAX}$ in the following manner. Assume the operator selects a nominal power of 25 watts. The voltage occuring across a 100 ohm load for this wattage corresponds to $V_{MAX}$, thus in this case $V_{MAX}$ would be 50 volts. As stated above $P_{MAX}$ occurs over the 70 to 100 ohm range. Further, the maximum voltage will occur with a 100 ohm load. Accordingly, $V_{MAX}$ is calculated in the foregoing manner. In general, $V_{MAX}=(100\ P_{MAX})^{\frac{1}{2}}=10(P_{MAX})^{\frac{1}{2}}$.

After the calculations of $V_{MAX}$ and $I_{MAX}$ COLDST applies a small control voltage AFB over line 19 to supply 10 to turn on RF generator 12 then waits for about 0.01 second to allow the RF output to become stable before transferring a control to the control routines, GETPWR 28 and CNTLP 30. GETPWR detects the load voltage signal $V_{SEN}$ occuring at line 15 and the load current signal $I_{SEN}$ occuring at line 17. The load power $P_{LOAD}$ is calculated as $V_{SEN} \cdot I_{SEN}$. Furthermore, the load impedance $Z_{LOAD}$ is calculated as $V_{SEN}/I_{SEN}$. A determination is also made as to which impedance range the load impedance occurs in. Thus, a first impedance range flag (not shown) is set if the load impedance range is less than 70 ohms, a second flag is set if it is between 70 and 100 ohms, and a third flag is set if it is above 100 ohms. It should be understood a substantial amount of tolerance may be employed in the selection of the impedance ranges. Thus, if desireable, the mid impedance range may extend from 60 to 115 ohms, for example.

As stated above the operator may select between one of two different modes in the high impedance range. Depending upon the selected mode, a further flag will be set by COLDST indicating the selected mode. The routine CNTLP inspects the above flags and determines which of the following algorithms should be executed. These algorithms are LOZ 32, MIDZ 36, ZOL 38, and HIZR2 40 as can be seen in FIG. 3. All of these algorithms eventually pass control to a routine AFBADJ 34. Each of these routines will now be individually discussed.

Assuming the load impedance is measured as 40 ohms, CNTLP will transfer control to LOZ 32. A correction factor will be computed which will implement the constant current characteristic described above for the low impedance range. In particular, if $I_{SEN}=1.2$ amps and if $I_{MAX}=1$ amp (for example), then the correction factor is computed as $I_{MAX}/I_{SEN}$. Thus, the calculated factor equals 1.0/1.2. After calculation of the correction factor control is passed to AFBADJ 34 which raises or lowers the control voltage AFB based on the computed correction factor. Thus, if the value of AFB is 10 volts, it will be reduced by the correction factor of 1.0/1.2. In this manner the current is maintained constant at the value of $I_{MAX}$ (1.0 amp) over the lower impedance range. Note in this example that $I_{SEN}$ exceeds $I_{MAX}$. Whether it exceeded it or not, the correction factor is calculated as $I_{MAX}/I_{SEN}$ over the entire low impedance range by the LOZ routine.

After the corrected control voltage is applied over line 19 to supply 10, a test is made to determine if the operator is still enabling the generator to apply electrosurgical power to the forceps. This test is conducted at 42. If the generator is so enabled, control is returned to GETPWR. Execution of the routines from GETPWR through AFBADJ requires at most about 20 milliseconds and thus the power delivered to the load is constantly being adjusted depending upon the sensed load conditions. If there are no more enables, the routine may return to an initialization mode where the output is set off and certain self-test routines are executed while waiting for the next enable. This feature is not shown in the flow chart of FIG. 3.

As stated above the impedance of the tissue will tend to increase as desiccation proceeds. Hence, assume the next load measured by the GETPWR routine is 80 ohms. The MIDZ flag would be set and the load power calculated. The routine CNTLP would again determine the actuated flags and transfer control to the MIDZ routine 36. There a correction factor is calculated in accordance with the expression $(P_{MAX}/P_{LOAD})^{\frac{1}{2}}$ where $P_{MAX}$ equals the nominal power selected by the operator and $P_{LOAD}=V_{SEN} \cdot I_{SEN}$ as calculated in GETPWR. Thus, if $P_{LOAD}$, the actual load power, is 60 watts and $P_{MAX}$ the nominal power is 70 watts, the calculated correction factor is $(7/6)^{\frac{1}{2}}$. Once this correction factor has been determined, control is passed to the AFBADJ routine 34 where the correction factor is multiplied by the previous value of control voltage AFB applied to line 19. The adjustment of the control voltage and the application over line 19 is executed in the same manner as described above for the LOZ routine.

With the passage of further time the impedance continues to increase. Thus, assuming the desiccation mode is still enabled by the operator, control will be returned to GETPWR and CNTLP. Further, assuming the operator has selected mode one for the high range impedances, CNTLP 30 will transfer control to ZOL 38 after having sensed the appropriate flags. If the impedance calculated by GETPWR is now 200 ohms, the power delivered to it will have a constant voltage characteristic as described above with respect to FIG. 2. In particular, the constant voltage will be $V_{MAX}$ as calculated by the COLDST routine. In order to implement this constant voltage characteristic ZOL calculates a correction factor determined by the expression $V_{MAX}/V_{SEN}$ where $V_{SEN}$ equals the load voltage sensed by GETPWR. If the sensed voltage is 70 volts while $V_{MAX}$ is 50 volts, the correction factor will be 5/7. AFBADJ utilizes this correction factor in the same manner as discussed above for LOZ and MIDZ to adjust the control voltage applied to line 19.

If the operator has selected mode 2, this will be sensed by the CNTLP together with the fact that the impedance is now in the high impedance range. Assume that the impedance at this time is 200 ohms while $P_{MAX}$ is 50 watts and $P_{LOAD}=60$ watts. The correction factor is computed as $[(10,000\ P_{MAX}/Z^2_{LOAD})/P_{LOAD}]^{\frac{1}{2}}$. Thus, in the above instance, it equals $[(10,000)(50)/(40,000)/60]^{\frac{1}{2}}=(5/24)^{\frac{1}{2}}$. Again, after computation of the correction, control is passed to AFBADJ to adjust the line 19 control voltage. Attached hereto as Appendix I is a program listing for the FIG. 3 flowchart where the listing also includes various initialization, testing, and error programs.

Figure 4A:
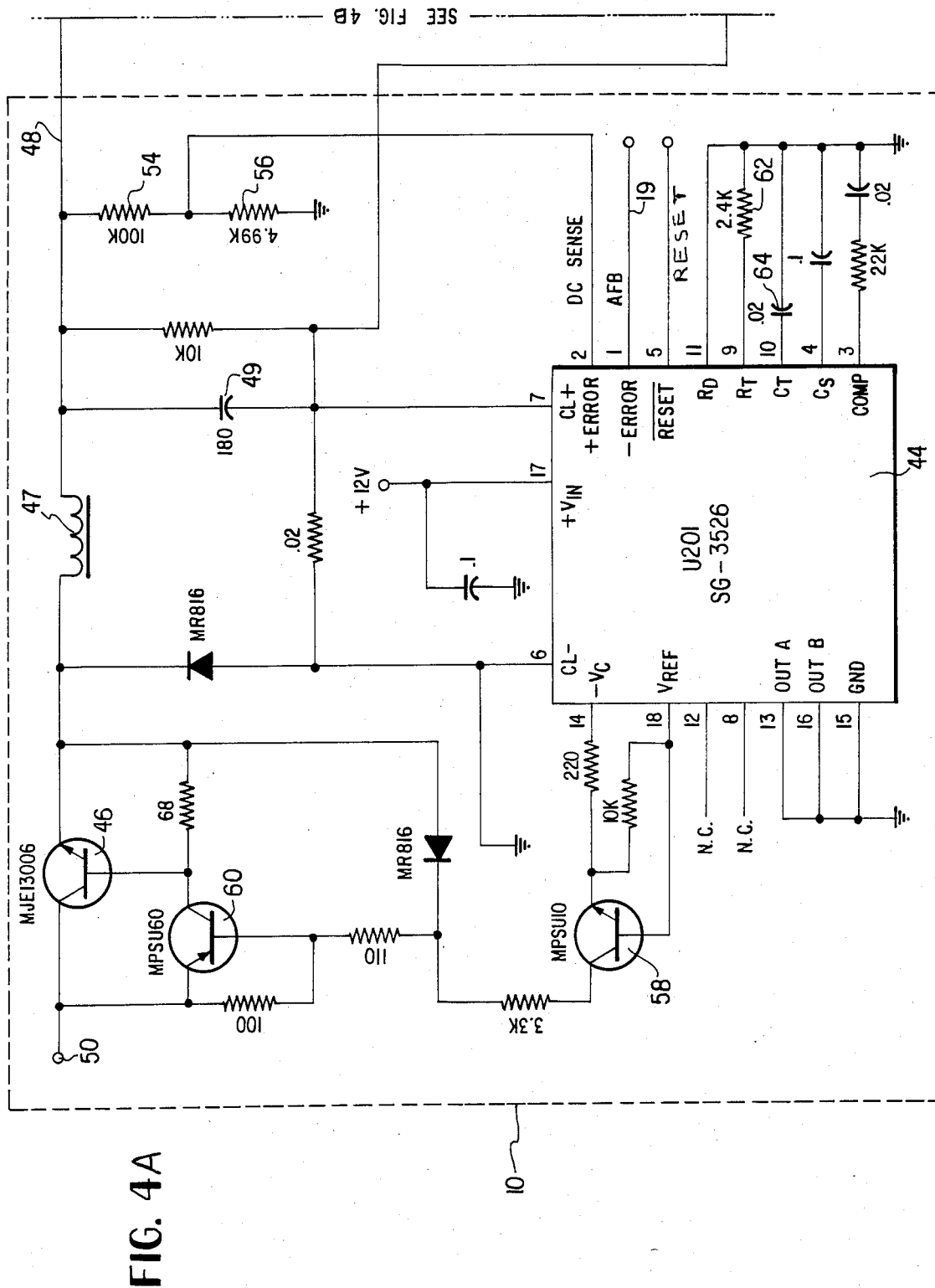
FIGS. 4A and 4B is a schematic diagram of the switching power supply, the generator and the voltage and current sensing circuitry of FIG. 1.
Figure 4B:
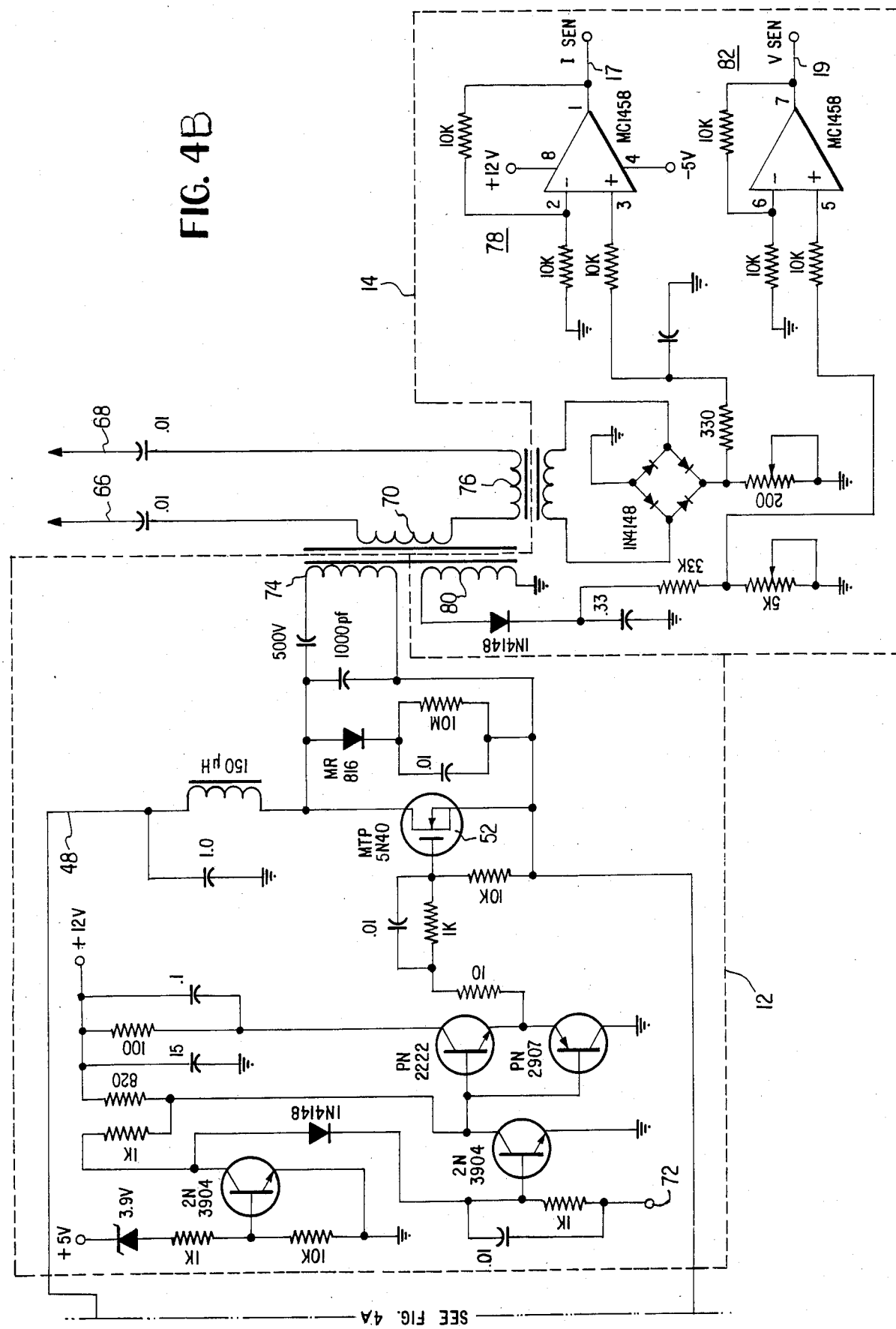

Reference should now be made to FIGS. 4A and 4B which is a schematic diagram of switching power supply 10, high efficiency RF generator 12, and current sensors 14 of FIG. 1. The switching power supply includes a standard switching supply circuit 44 made by Silicon General. The remaining integrated circuits of the invention are also made by Silicon General and other such companies. The switching power supply is of conventional configuration and includes a switching transistor 46 and inductor 47, and an output line 48 which applies regulated high voltage to output transistor 52 of generator 12. The power supply voltage applied to line 48 originates from terminal 50, this voltage typically being about 100 volts. The voltage at terminal 50 is regulated by switching transistor 46, inductor 47 and capacitor 49 where, in particular, the longer transistor 46 is switched off, the less the DC voltage applied to line 48 will be in magnitude. A voltage DC SENSE proportional to the line 48 voltage is applied to terminal 2 of circuit 44 via a voltage divider comprising resistors 54 and 56. This voltage is compared to and follows AFB on line 19.

On-off pulses are applied to switching transistor 46 from circuit 44 via transistors 58 and 60. The repetition rate of these pulses is determined by resistor 62 and capacitor 64 connected to the $R_T$ and $C_T$ terminals of circuit 44. The width of these pulses and thus the on/off time of transistor 46 is a function of the difference between AFB and DC SENSE. Thus, in this manner the power supply voltage follows AFB as the impedance changes during a desiccation procedure.

The output power is delivered to the load via lines 66 and 68 which in turn are connected to output transformer 70. The generator 12 is driven by a 750 KHz signal applied to terminal 72 where it is amplified and applied to output transistor 52 which in turn drives primary winding 74 of transformer 70.

The load current is sensed at transformer 76 and converted to a voltage representative of the current by the conversion circuitry indicated at 78. This voltage is applied over line 17 as the $I_{SEN}$ signal to the microprocessor 16. Furthermore, a voltage representative of the load voltage is derived from winding 80 of transformer 70. This signal is converted by signal conversion circuitry 82 to develop the load voltage at $V_{SEN}$ on line 19.

The values given for the resistors are in ohms while those for the capacitances are microfarads unless otherwise specified, these values being illustrative of the embodiment of the invention.

It should be noted that overall operation of the present invention is such that a very small heat sink is needed to dissipate heat, thus, a 3-4 watt sink connected to transistor 52 is suitable, such a sink being very small in size. This follows from the fact that the amplifier is essentially matched to a 100 ohm load and only in a limited impedance range around that value is the maximum delivered to the load.

With the load impedance substantially removed from 100 ohms, the power is reduced as discussed above and shown in FIG. 2. There is no need to generate substantial wattage at impedances removed from the impedance to which the amplifier is matched. Accordingly, even at impedances removed from 100 ohms only a small amount of power is involved whereby the small heat sink mentioned above is suitable for these smaller powers.

It is to be understood that the above detailed description of an embodiment of the invention is provided by way of example only. Thus, for example, the above principles are also applicable to monopolar surgery. Various details of design and construction may be modified without departing from the true spirit and scope of the invention as set forth in the appended claims.

APPENDIX I

```
1
2                                   TITLE    'SSE4 BIPOLAR CONTROL:22 NOVEMBER 1982:CHECKSUM C730
3                                *  TABLE SETS UP STORAGE LOCATIONS FOR RAM
4                                *
6  -                                NLIST   M
7                                   ORG 20H
8   0020                   ECON     DS      1
9   0021                   VSEN     DS      1
10  0022                   ISEN     DS      1
11  0023                   UCSEN    DS      1
12  0024                   Z        DS      1              IMPEDANCE OF LOAD,3.125OHMS/COUNT
13  0025                   ZRANGE   DS      1
14  0026                   POWER    DS      1
15  0027                   PREQ     DS      1              COMPUTED NECESSARY POWER
16  0028                   AFB      DS      1
17  0029                   CORECT   DS      1              CORRECTION FACTOR ON POWER
```

```
18   002A              RTECON   DS     1
19   002B              IMAX     DS     1
20   002C              VMAXR2   DS     1
21   002D              P1MAGE   DS     1                PORT 1 IMAGE
22   002E              DWNCNT   DS     1                COUNT OF # OF CONSECUTIVE DOWN COUNTS
23   002F              MODES    DS     1                KEYING INPUTS 0,DSE,DS1F,DS2E
24   0008              DAC      EQU    08H
25   0000              CHECK    EQU    R5
26   002B              VMAXR1   EQU    IMAX
27   0000              COUNT    EQU    R3
28   0008              DOG      EQU    8
29   0001              KEY      EQU    1
30   0002              RESET    EQU    2
31   0004              SDN      EQU    4
32   0010              IFLAG    EQU    16
33   0020              VFLAG    EQU    32
34   0040              MAXD     EQU    64
35   0080              ERLITE   EQU    128
37                     *
38                     *        MACRO DEFINITIONS FOLLOW:
39                     *        RECALL GETS FROM RAM STORAGE AN 8 BIT VALUE
40                     *        AND LOADS IT IN ACCUMULATOR.
41                     *        IF P=0, NOTHING ELSE IS DONE.
42                     *        IF P=1, THEN THE VALUE IS MOVED TO REGISTER RP.
43                     *        FORMAT:
44                     *                 RECALL   ECON,0
45                     *        OR
46                     *                 RECALL   VSEN,1,R4
47
48              RECALL          MACRO    VAL,P,RP
49                              MOV      R1,#VAL
50                              MOV      A,@R1
51                              IF       P
52                              MOV      RP,A
53                              ENDIF
54                              ENDM
57                     *********************
58                     *
59                     *        MACRO STORE
60                     *        TAKES A VALUE FROM (1) THE ACCUMULATOR IF R=0
61                     *
62                     *        OR FROM THE REGISTER RP IF R=1
63                     *        AND STORES IT IN LOCATION VAL.
64                     *
65                     *        FORMAT:
66                     *                 STORE    ISEN,0
67                     *        OR
68                     *                 STORE    POWER,1,R5
69                     *
70                     *
72              STORE           MACRO    VAL,R,RP
73                              MOV      R1,#VAL
74                              IF       R
75                              MOV      A,RP
76                              ENDIF
77                              MOV      @R1,A
78                              ENDM
79                     *
80                     *        MACRO ROUND   ROUNDS UP THE ACCUMULATOR BASED ON MSB OF REGISTER
81                     *        FORMAT
82                     *                 ROUND    RA
83                     *
84              ROUND           MACRO    RX
85                              XCH      A,RX
86                              RLC      A                CARRY=ROUNDUP
87                              CLR      A
88                              ADDC     A,RX
89                              ENDM
92                     ***************************
93                     *
94                     *        ADC IS A MACRO WHICH
95                     *        TAKES CARE OF THE A TO D CONVERSION
96                     *        AND STORAGE FOR THE ANALOG INPUTS.
97                     *
98                     *        FORMAT: ADC              ECON
99                     *
100                    ***************************
101             ADC             MACRO    WHAT
102                             LOCAL    WHERE
103                             LOCAL    WHO
104                             MOV      R1,#WHAT-20H
105                             MOV      R0,#WHAT
106                             MOVX     @R1,A            START CONVERSION
107                             MOV      R3,#8
108             WHO             DJNZ     R3,WHO           WAIT FOR EOC TO GO DOWN
109                             JNI      WHERE
110                             JMP      $-2              WAITING FOR INTERRUPT
111             WHERE           MOVX     A,@R1
112                             MOV      @R0,A            STORE THE RESULT
113                             ENDM
115                    ***************************
116                    *
117                    *        WAIT IS A SIMPLE DELAY LOOP
118                    *        USING REGISTERS 3 AND 4
119                    *
120                    *        CALLED BY THE COMMAND
121                    *
122                    *        WAIT     N
123                    *        WHERE N IS ANY INTEGER LESS THAN 256
124                    *        WILL DELAY 256*2*N MACHINE CYCLES.
125                    ***************************
```

```
WAIT      MACRO    N
          IF       N
          MOV      R4,#N
          DJNZ     R3,S
          DJNZ     R4,S-2
          ELSE
          NOP
          NOP
          NOP
          NOP
          NOP
          NOP
          ENDIF
          ENDM
**********************************
*
*
*         THIS IS A SIMPLE MINDED ROUTINE
*         WHICH RESETS THE WATCHDOG TIMER.
*
**********************************

WCHDOG    MACRO
          ORL      P1,#DOG
          WAIT     2
          ANL      P1,#255-DOG    WCHDOG=0
          WAIT     2
          ENDM
**********************************
*
*         ROM CHECKSUM ROUTINE
*
*         THIS ROUTINE SUMS UP ALL POSSIBLE ROM LOCATIONS
*         AND IF THE ANSWER IS NOT ZERO, JUMPS OUT TO
*         ERROR: WHICH HANGS UP THE PROCESSOR.
*
**********************************

ROMCHK    MACRO    Q,R
          LOCAL    LOOPA
          MOV      COUNT,#00
LOOPA     MOV      A,COUNT
          MOVP     A,@A
          ADD      A,CHECK
          MOV      CHECK,A
          DJNZ     COUNT,LOOPA
          IF       Q-1
          JMP      R              NEXT RUMCH
          ELSE
          RET
          ENDIF
          ENDM
**********************************
*
*         SUBTR
*
*         SUBTRACTS A REGISTER FROM
*         THE ACCUMULATOR IN 2S COMPLEMENT
*         NOTATION
*         CARRY SET IF ANSWER IS POSITIVE
*
**********************************
SUBTR     MACRO    RX
          LOCAL    WHO
          XCH      A,RX
          JNZ      WHO
          INC      A
          INC      RX
WHO       CPL      A
          INC      A              2S COMPLEMENT A
          ADD      A,RX
          ENDM
**********************************
*
*    PORT MACRO
*    WRITES TO PORT ONE, WITH THE
*    VALUE OF KEY, SHUTDOWN OR RESET DESIRED.
*
*    FORMAT
*    PORT     KEY,1
*    OR,
*    PORT     SDN,0
*
**********************************

PORT      MACRO    WHAT,N
          RECALL   P1MAGE,0
          IF       N
          ORL      A,#WHAT
          ELSE
          ANL      A,#255-WHAT
          ENDIF
          OUTL     P1,A
          STORE    P1MAGE,0
          ENDM
*ENDMACROS*
**********************************
*
*         INITIALIZATION
*
*         CLEAR THE OUTPUTS AND DAC
```

```
231                    *       RESET THE WATCHDOG
232                    *       RUN ROMCHK AND RAMCHK
233                    *       AND LOOK FOR KEYING INPUTS
234                    *
235              ***********************************
236                    *
237                    *
238                            ORG       00
239   0000  75   INIT          ENTO      CLK
240   0001  15                 DIS       I
241   0002  B9 08              MOV       R1,#08H
242   0004  27                 CLR       A
243   0005                     STORE     AFB,0
249   0008  91                 MOVX      @R1,A         CLEAR THE DAC
250   0009                     WCHDOG
279   0019                     PORT      KEY,1
298   0022                     PORT      SDN,0         NO KEY, SHUTDOWN
317   0029                     PORT      RESET,0       RESETNOT IS ASSERTED HERE
337              *******************************
338                    *
339                    *       RAMCHK ROUTINE
340                    *
341                    *       THIS ROUTINE WRITES 00,THEN FFH TO R0 TO CHECK IT
342                    *
343                    *       THEN WRITES 00 THEN FFH TO EACH RAM LOCATION IN SUCCESSION.
344                    *       IF A READ OR WRITE IS NUT ACCOMPLISHED,
345                    *       THE ROUTINE JUMPS OUT TO ERROR
346                    *         WHICH SHUTS DOWN ALL PORTS AND HANGS THE PROCESSOR.
347                    *
348              *******************************
350   0034  B8 FF  RAMCHK       MOV       R0,#0FFH      ALL 1S TO R0
351   0036  F8                  MOV       A,R0
352   0037  37                  CPL       A
353   0038  C6 3C               JZ        $+4
354   003A  44 23               JMP       ERROR         ALL 1S ERROR
355   003C  A8                  MOV       R0,A
356   003D  F8                  MOV       A,R0
357   003E  C6 42               JZ        $+4
358   0040  44 23               JMP       ERROR
359   0042  B8 7F               MOV       R0,#07FH      TOP RAM LOCATION
360   0044  37                  CPL       A
361   0045  A0     LOOP6        MOV       @R0,A         ALL ONES IN A
362   0046  F0                  MOV       A,@R0
363   0047  37                  CPL       A             A NOW HAS ALL ZEROS
364   0048  C6 4C               JZ        $+4
365   004A  44 23               JMP       ERROR
366   004C  A0                  MOV       @R0,A
367   004D  F0                  MOV       A,@R0
368   004E  C6 52               JZ        $+4
369   0050  44 23               JMP       ERROR
370   0052  37                  CPL       A             ALL ONES BACK IN A
371   0053  E8 45               DJNZ      R0,LOOP6      DEC RAM LOC AND CONTINUE
372   0055  23 01               MOV       A,#0001B      SDN,RESETNUT,KEYNOT
373   0057                      STORE     PIMAGE,0      RESTORE PIMAGE TO INITIAL COX
379   005A  39                  OUTL      P1,A          AND WRITE TO PORT
381                    *
382                    *       THIS IS A SEQUENCE OF ROMCHECK
383                    *       ROUTINES, ONE FOR EACH PAGE OF MEMORY.
384                    o
385                    *       NOW THE CALLUP FOR THE MAIN ROMCHK ROUTINE.
386                    *
387                    o
388   005B  23 00  ROM          MOV       A,#00
389   005D  A0                  MOV       CHECK,A
390   005E  04 61               JMP       LOOPB
391   0060  AD                  DB        0ADH          THIS IS THE CHECKSUM CORRECTOR
392   0061  14 F0  LOOPB        CALL      ROMST
393   0063  C6 65  ENDINT       JZ        COLDST        EVERYTHING OK HERE
394   0065  C4 82               JMP       KILL6         IF CHECKSUM NOT ZERO
395                    *       NOW DO ALL THE LITTLE ROMCHECKS.
396                    *
397                    *
398                            ORG       0F0H
399   00F0   ROMST              ROMCHK    0,ROM1
411                            ORG       01F4H
412   01F4   ROM1               ROMCHK    0,ROM2
424                            ORG       02F0H
425   02F0   ROM2               ROMCHK    0,ROM3
437                            ORG       03F4H
438   03F4   ROM3               ROMCHK    0,ROM4
450                            ORG       04F0H
451   04F0   ROM4               ROMCHK    0,ROM5
463                            ORG       05F0H
464   05F0   ROM5               ROMCHK    0,ROM6
476                            ORG       06F0H
477   06F0   ROM6               ROMCHK    0,ROM7
489                            ORG       07F0H
490   07F0   ROM7               ROMCHK    1,ROM8        BACK TO MAIN ROUTINE
503              *******************************
504                    *
505                    *       COLDST ROUTINE
506                    o
507                    *       WHICH BRINGS THE MACHINE UP FROM A COLD START
508                    *       TO AN INITIAL VALUE OF 5 VOLTS.
509              *******************************
511                            ORG       ENDINT+2
512   0065   COLDST             WCHDOG
541   0075  85                  CLR       F0            RANGE 1 SETUP
```

```
542  0076  B8 08              MOV    R0,#DAC        SET DAC VOLTS TO ZERO
543  0078  27                 CLR    A
544  0079  90                 MOVX   @R0,A
545  007A  0A                 IN     A,P2
546  007B  53 70              ANL    A,#70H         DSE,DS2E,DS1E
547  007D                     STORE  MODES,0
553  0080  C6 65              JZ     COLDST         WAITING FOR INPUT
554  0082  AD                 MOV    R5,A           TEMP STORAGE OF ENABLES
555  0083  D3 70              XRL    A,#70H         ALL THREE MEAN TESTLOOP
556  0085  C6 93              JZ     TST
557  0087  FD                 MOV    A,R5           GETS ORIG.DATA BACK
558  0088  D3 60              XRL    A,#60H         DSE AND DS2E
559  008A  C6 95              JZ     RA2
560  008C  FD                 MOV    A,R5
561  008D  D3 50              XRL    A,#50H         DSE AND DS1E
562  008F  C6 96              JZ     RA1
563  0091  04 65              JMP    COLDST         IF INVALID INPUTS
564  0093  E4 00       TST    JMP    TESTLP
565  0095  95          RA2    CPL    F0             SETS RANGE2 FLAG
566  0096              RA1    ADC    ECON
576  00A5  03 25              ADD    A,#37
577  00A7  E6 AA              JNC    TMP
578  00A9  27                 CLR    A
579  00AA  03 D6       TMP    ADD    A,#219         RESTORE A TO 219 MAX
580  00AC  A0                 MOV    @R0,A          STORE THE NEW ECON
581  00AD  74 8C              CALL   SORT           SQUARE ROOT ROUTINE ON ECON
582  00AF                     STORE  RTECON,0       RA HAS RTECON
589
590         *
591         *         NOW COMPUTE IMAX AND VMAX AND VMAXR2
592         *
593         ************************
595  00B2  AE                 MOV    R6,A
596  00B3  BC 08              MOV    R4,#008H
597  00B5  74 50              CALL   MUL
598  00B7  2A                 XCH    A,R2
599  00B8                     ROUND  R2
604  00BC                     STORE  IMAX,0         MAX ALLOWABLE CURRENT
610         *NOTE THAT VMAXR1 AND IMAX ARE REALLY THE SAME
611         *
612         *ONE AMPERE IS 200COUNTS, SO IS ONE HUNDRED VOLTS.
613  00BF  FE                 MOV    A,R6
614  00C0  77                 RR     A
615  00C1  67                 RRC    A
616  00C2  53 3F              ANL    A,#3FH
617  00C4  13 00              ADDC   A,#0           ROUNDUP
618  00C6                     STORE  VMAXR2,0       MAX 1/K**2 VOLTAGE
624  00C9  23 0A              MOV    A,#10
625  00CB                     STORE  AFB,0          5 VOLTS IS AFBSET
631  00CE  B8 08              MOV    R0,#DAC        DAC OUTPUT ADDRESS
632  00D0  90                 MOVX   @R0,A          WRITE AFB
633  00D1                     PORT   KEY,0
652  00DA                     PORT   RESET,1        RESETNOT NOT ASSERTED
671  00E3                     WAIT   10H
684  00E9  24 00              JMP    GETPWR
685         *         NOW DO GETPWR FOR CLOSED LOOP
           ************************
687
688         *
689         *         GETPWR ROUTINE
690         *
691         *         MEASURES V,I
692         *         COMPUTES Z
693         *         DETERMINES ZRANGE
694         *
695         *         ZRANGE IS A WORD INTERPRETED
696         *         OVOLT,OCCUR,VMAX,IMAX,ZOL,HIZ,MIDZ,LOZ
697         *
698         *         DETERMINES OUTPUT POWER
699         *
700         *         CALLS THE CONTROL LOOP
701         *
702         ************************
704                            ORG    100H
705  0100  27          GETPWR CLR    A
706  0101  AE                 MOV    R6,A           R6 IS TEMP ZRANGE REGISTER
707  0102                     ADC    VSEN
717  0111  AA                 MOV    R2,A
718  0112  AD                 MOV    R5,A           TEMP SAVE VSEN
719  0113  F2 20              JB7    VFL            IF V>64 VLITE ON
720  0115                     PORT   VFLAG,0        ELSE,LITE OFF
739  011E  24 29              JMP    CKV
740  0120              VFL    PORT   VFLAG,1
759  0129  FD          CKV    MOV    A,R5           GETS V BACK
760  012A  03 37              ADD    A,#55
761  012C  E6 32              JNC    CKVMX          CARRY IF OVOLTS
762  012E  2E                 XCH    A,R6
763  012F  43 80              ORL    A,#80H         OVERVOLTS FLAG
764  0131  2E                 XCH    A,R6
765  0132              CKVMX  RECALL VMAXR1,0
771  0135  37                 CPL    A              -VMAXR1
772  0136  17                 INC    A              2S COMPLEMENT
773  0137  6A                 ADD    A,R2           VSEN-VMAXR1,CARRY IF POSITIVE
774  0138  E6 3E              JNC    GETI
775  013A  2E                 XCH    A,R6
776  013B  43 20              ORL    A,#20H
777  013D  2E                 XCH    A,R6
778  013E              GETI   ADC    ISEN
788  0140  AC                 MOV    R4,A
```

```
789  014E  F2 5B         JB7     IFL            TURN ON ILITE IF I>640
790  0150                PORT    IFLAG,0        ELSE OFF
809  0159  24 64         JMP     CKI
810  015B          IFL   PORT    IFLAG,1
829  0164  FC      CKI   MOV     A,R4           GETS I BACK
830  0165  03 37         ADD     A,#55
831  0167  E6 6D         JNC     HOUSE          CARRY IF I>1A
832  0169  2E            XCH     A,R6
833  016A  43 40         ORL     A,#40H          OCCURRENT FLAG
834  016C  2E            XCH     A,R6            SAVE ZRANGE
835  016D          HOUSE RECALL  IMAX,0
841  0170  37            CPL     A              -IMAX
842  0171  17            INC     A              2S COMPLEMENT
843  0172  6C            ADD     A,R4           ISEN=IMAX,CARRY IF POSITIVE
844  0173  E6 79         JNC     HOUSE1
845  0175  2E            XCH     A,R6
846  0176  43 10         ORL     A,#10H          SET IMAX FLAG
847  0178  2E            XCH     A,R6
848  0179  27      HOUSE1 CLR    A
849  017A  97            CLR     C              HOUSEKEEPING
850  017B  B8 06         MOV     COUNT,#06
851  017D  2A      LOOP1 XCH     A,R2
852  017E  67            RRC     A
853  017F  E8 7D         DJNZ    COUNT,LOOP1    DIVIDES R2 BY 8
854  0181  74 6D         CALL    DIV            R2:A/R4=V/I/8
855  0183                STORE   Z,0
861  0186  E6 8E         JNC     LOOP2          CARRY IF Z>800
862  0188  2E            XCH     A,R6
863  0189  43 08         ORL     A,#8           HIGH Z FLAG
864  018B  2E            XCH     A,R6
865  018C  24 A6         JMP     ZRSTO
866  018E  03 DF   LOOP2 ADD     A,#223         CARRY IF Z>100 OHMS
867  0190  E6 98         JNC     MIDZ
868  0192  2E            XCH     A,R6
869  0193  43 04         ORL     A,#04
870  0195  2E            XCH     A,R6
871  0196  24 A6         JMP     ZRSTO
872  0198  03 0A   MIDZ  ADD     A,#10          CARRY IF Z>70 OHMS
873  019A  E6 A2         JNC     LOZ
874  019C  2E            XCH     A,R6
875  019D  43 02         ORL     A,#2
876  019F  2E            XCH     A,R6           SETS LOZ FLAG
877  01A0  24 A6         JMP     ZRSTO
878  01A2  2E      LOZ   XCH     A,R6
879  01A3  43 01         ORL     A,#1
880  01A5  2E            XCH     A,R6
881  01A6          ZRSTO STORE   ZRANGE,1,R6
887  01AA  FD            MOV     A,R5           VOLTS FOR POWER COMP
888  01AB  74 50         CALL    MUL            R4*A GOES TO R2:A
889  01AD  97            CLR     C
890  01AE  F7            RLC     A              POWER BIT 7 IN CARRY
891  01AF  2A            XCH     A,R2           BITS 15-8 IN A
892  01B0  F7            RLC     A              2 TIMES POWER
893  01B1                ROUND   R2
898  01B5                STORE   POWER,0
904  01B8  44 00         JMP     CNTLP
906                *************************************
907                *
908                *       CNTLP
909                *
910                *       ONCE WE HAVE THE POWER AND IMPEDANCE INFORMATION
911                *       THIS ROUTINE DECIDES WHAT FEEDBACK MODE TO USE.
912                *
913                *************************************
915                      ORG     200H
916  0200          CNTLP RECALL  ZRANGE,0       OVOLT,OCCUR,VMAX,IMAX,ZOL,HIZ,MIDZ,LOZ
922  0203  C6 23         JZ      ERROR          ZRANGE NUMBER SHOULDNT BE ZERO
923  0205  F2 1F         JB7     OVOLT          V>100
924  0207  02 21         JB6     OCCUR          I>1
925  0209  92 27         JB4     CLOZ           I>IMAX
926  020B  82 17         JB5     VMAX
927  020D  12 27   LOOP2 JB0     CLOZ
928  020F  32 33         JB1     CMIDZ          MID RANGE CALC.
929  0211  72 25         JB3     ZOL            Z>800
930  0213  86 3B         JF0     HIZR2          Z>100 AND RANGE 2
931  0215  44 25         JMP     ZOL            ELSE,Z>100 AND RANGE1
932  0217  86 1B   VMAX  JF0     VMAX2          V>VMAX,AND RANGE2
933  0219  44 25         JMP     ZOL            HIZ TREATMENT R1
934  021B  52 3B   VMAX2 JB2     HIZR2          IF 100<Z<500
935  021D  44 0D         JMP     LOOP2          BACK UP TO MAIN LOOP
936  021F  84 00   OVOLT JMP     OVOLT4         OVOLT IS ON PAGE 4
937  0221  84 47   OCCUR JMP     OCCUR4
938  0223  A4 0D   ERROR JMP     ERROR5         DITTO OCCUR AND ERROR
939  0225  44 58   ZOL   JMP     ZOL2           ZOL2 ON PAGE 2
941                *************************************
942                *
943                *       CLOZ ROUTINE
944                *
945                *       COMPUTES F1.CORECT WHERE
946                *       F1=1 OR 0 AND CORECT IS LESS THAN 1
947                *
948                *       ROUTINE USES THE LAST HALF OF THE
949                *       HIZ ROUTINE FOR COMMONALITY
950                *
951                *************************************
953  0227  A5      CLOZ  CLR     F1             DOWN FLAG
954  0228                RECALL  ISEN,1,R4
960  022C  AB            MOV     R3,A           SAVE ISEN
```

```
 961  0220               RECALL    IMAX,1,R2
 967  0231  44 68        JMP       R2ZOL          REST OF ROUTINE IS COMMON
 968                                               WITH ZOL ROUTINE
 970      *******************************
 971      *
 972      *        ROUTINE MID Z
 973      *        SETS PREQ EQUAL TO ECON
 974      *        WHICH IS TRUE,MORE OR LESS
 975      *
 976      *******************************
 977      *
 979  0233      CMIDZ    RECALL    ECON,0
 985  0236               STORE     PREQ,0
 991  0239  84 88        JMP       POWCOM
 993      *******************************
 994      *
 995      *                 HIZ
 996      *
 997      *        THIS ROUTINE COMPUTES POWER PREQ
 998      *        FOR THE HIGH IMPEDANCE REGION AND THE
 999      *        1/R**2 MODE
1000      *
1001      *******************************
1003  023B      HIZR2    RECALL    Z,1,R4
1009  023F 74 50         CALL      MUL             R2=Z**2
1010  0241 F7             RLC       A
1011  0242 27             CLR       A
1012  0243 7A             ADDC      A,R2            A=Z**2+ROUNDUP
1013  0244 AC             MOV       R4,A
1014  0245               RECALL    ECON,0
1020  0248 97             CLR       C
1021  0249 BA 00          MOV       R2,#00
1022  024B B9 04          MOV       COUNT,#04
1023  024D F7    LOOPS    RLC       A
1024  024E 2A             XCH       A,R2
1025  024F EB 4D          DJNZ      COUNT,LOOPS
1026  0251 74 66          CALL      DIV
1027  0253               STORE     PREQ,0
1033  0256 84 88          JMP       POWCOM
1035      *******************************
1036      *
1037      *        ROUTINE ZOL
1038      *
1039      *        AIMS FOR A CONSTANT VOLTAGE
1040      *        VMAXR1 OR VMAXR2 AS SET BY F0
1041      *        CORECT IS F1.CORECT WHERE F1 IS 1 OR 0
1042      *        CORECT IS A VALUE LESS THAN 1
1043      *
1044      *        CORECT=VREQ/VOUT
1045      *
1046      *******************************
1048  0258 A5   ZOL2      CLR       F1              DOWN FLAG
1049  0259               RECALL    VSEN,1,R4
1055  025D AB             MOV       R3,A            SAVE VSEN
1056  025E               RECALL    VMAXR2,1,R2     IF RANGE 2
1062  0262 86 68          JF0       R2ZOL
1063  0264               RECALL    VMAXR1,1,R2     IF I/R RANGE
1069  0268     R2ZOL     SUBTR     R3              A=VMAX-VSEN,CARRY IF POS
1077  0270 E6 74          JNC       NEWSET          IF NEG,DIVIDE R2/R4
1078  0272 85             CPL       F1              POSITIVE ANSWER,CORECT>1
1079  0273 2A             XCH       A,R2            VMAX-VSEN IN R2
1080  0274 27   NEWSET    CLR       A               R2:00/R4
1081  0275 74 66          CALL      DIV
1082  0277 E6 7B          JNC       CORGET
1083  0279 23 FF          MOV       A,#0FFH         NEED LOTS VOLTS
1084  027B     CORGET    STORE     CORECT,0
1090  027E C4 00          JMP       AFBADJ
1092      *HERE IS THE DATA FILE
1093      *CONTAINING RTECON BASE
1094      *FOR ALL #S FROM 0 TO 256 IN
1095      *INCREMENTS OF 4
1096                     ORG       300H
1097  0300 00            DB        00
1098  0301 20 2D 37 40   DB        32,45,55,64
1099  0305 48 4E 55 5B   DB        72,78,85,91
1100  0309 60 65 6A 6F   DB        96,101,106,111
1101  030D 73 78 7C 80   DB        115,120,124,128
1102  0311 84 88 8B 8F   DB        132,136,139,143
1103  0315 93 96 99 9D   DB        147,150,153,157
1104  0319 A0 A3 A6 A9   DB        160,163,166,169
1105  031D AC AF B2 B5   DB        172,175,178,181
1106  0321 B8 BB BD C0   DB        184,187,189,192
1107  0325 C3 C5 C8 CA   DB        195,197,200,202
1108  0329 CD CF D2 D4   DB        205,207,210,212
1109  032D D7 D9 DB DE   DB        215,217,219,222
1110  0331 E0 E2 E5 E7   DB        224,226,229,231
1111  0335 E9 EB ED EF   DB        233,235,237,239
1112  0339 F2 F4 F6 F8   DB        242,244,246,248
1113  033D FA FC FE FF   DB        250,252,254,255
1115      *******************************
1116      *
1117      *        MULTIPLY ROUTINE (8 X 8)
1118      *
1119      *******************************
1120      *
1121      *        IN:  A = MULTIPLICAND
1122      *             R4 = MULTIPLIER
```

```
1123                          *                                           *
1124                          *     OUT: A = LOWER 8 BITS OF PRODUCT      *
1125                          *          R2 = UPPER 8 BITS OF PRODUCT     *
1126                          *                                           *
1127                          *********************************************
1128
1129                                   ORG       0350H
1130   0350  BA 00            MUL     MOV       R2,#00
1131   0352  B8 08                    MOV       R3,#8
1132   0354  12 5E            MPY8LP  JB0       MPY8A
1133   0356  2A                       XCH       A,R2
1134   0357  97                       CLR       C
1135   0358  67                       RRC       A
1136   0359  2A                       XCH       A,R2
1137   035A  67                       RRC       A
1138   035B  EB 54                    DJNZ      R3,MPY8LP
1139   035D  83                       RET
1140   035E  2A               MPY8A   XCH       A,R2
1141   035F  6C                       ADD       A,R4
1142   0360  67                       RRC       A
1143   0361  2A                       XCH       A,R2
1144   0362  67                       RRC       A
1145   0363  EB 54                    DJNZ      R3,MPY8LP
1146   0365  83                       RET
1147                          *********************************************
1148                          *                                           *
1149                          *                                           *
1150                          *        DIVIDE ROUTINE (16 X 8 BITS)       *
1151                          *                                           *
1152                          *********************************************
1153                          *                                           *
1154                          *     IN:  A = (R2:A) / R4                  *
1155                          *                                           *
1156                          *     OUT: A = QUOTIENT                     *
1157                          *          R2 = REMAINDER                   *
1158                          *                                           *
1159                          *********************************************
1160
1161   0366  2A               DIV     XCH       A,R2
1162   0367  B8 08                    MOV       R3,#8
1163   0369  37                       CPL       A
1164   036A  6C                       ADD       A,R4
1165   036B  37                       CPL       A
1166   036C  F6 71                    JC        DIVIA
1167   036E  A7                       CPL       C
1168   036F  04 8A                    JMP       DIVIB
1169   0371  6C               DIVIA   ADD       A,R4
1170   0372  97               DIVILP  CLR       C
1171   0373  2A                       XCH       A,R2
1172   0374  F7                       RLC       A
1173   0375  2A                       XCH       A,R2
1174   0376  F7                       RLC       A
1175   0377  E6 7E                    JNC       DIVIE
1176   0379  37                       CPL       A
1177   037A  6C                       ADD       A,R4
1178   037B  37                       CPL       A
1179   037C  64 86                    JMP       DIVIC
1180   037E  37               DIVIE   CPL       A
1181   037F  6C                       ADD       A,R4
1182   0380  37                       CPL       A
1183   0381  E6 86                    JNC       DIVIC
1184   0383  6C                       ADD       A,R4
1185   0384  64 87                    JMP       DIVID
1186   0386  1A               DIVIC   INC       R2
1187   0387  EB 72            DIVID   DJNZ      R3,DIVILP
1188   0389  97                       CLR       C
1189   038A  2A               DIVIB   XCH       A,R2
1190   038B  83                       RET
1191
1192                          *********************************************
1193                          *                                           *
1194                          *        SORT ROUTINE                       *
1195                          *                                           *
1196                          *     THIS ROUTINE COMPUTES THE             *
1197                          *     SQUARE ROOT OF THE VALUE IN THE ACCUMULATOR
1198                          *     BY USING A 6BIT LOOKUP AND LINEAR INTERPOLATION
1199                          *     RETURNS THE VALUE IN THE ACCUMULATOR  *
1200                          *                                           *
1201                          *                                           *
1202                          *********************************************
1203
1204   038C  A9               SORT    MOV       R5,A      HOLD X FOR LATER
1205   038D  77                       RR        A
1206   038E  77                       RR        A
1207   038F  53 3F                    ANL       A,#03FH   6BITS OF X
1208   0391  AE                       MOV       R6,A
1209   0392  17                       INC       A         BASE ADDR +1
1210   0393  E3                       MOVP3     A,@A      LOOKUP RTECON BASE+1
1211   0394  2E                       XCH       A,R6      R6=BASE RTECON+1
1212   0395  E3                       MOVP3     A,@A      RTECON
1213   0396  AA                       MOV       R2,A      SAVE THE BASE
1214   0397  37                       CPL       A         NEGATE BASE
1215   0398  17                       INC       A         TWOS COMPLEMENT
1216   0399  6E                       ADD       A,R6      BASE+1 MINUS BASE
1217   039A  AC                       MOV       R4,A      R4 HAS DIFF
1218   039B  FD                       MOV       A,R5      X
1219   039C  53 03                    ANL       A,#03H
1220   039E  C6 A5                    JZ        LOOPE
1221   03A0  AB                       MOV       R3,A
1222   03A1  27                       CLR       A
1223   03A2  6C               LOOPF   ADD       A,R4      SUM THE DIFF
1224   03A3  EB A2                    DJNZ      R3,LOOPF  1,2,OR 3 TIMES
```

```
1225  03A5  77                LOOPE    RR      A
1226  03A6  67                         RRC     A              DIFF/4,CARRY IN CARRY.
1227  03A7  53 3F                      ANL     A,#3FH
1228  03A9  7A                         ADDC    A,R2           A=KTECON BASE + INTERP.+CARRY
1229  03AA  83                         RET 1231
1232                          **************************************
1233                          *
1234                          *        OVOLT ROUTINE
1235                          *
1236                          *        CALLED FROM GETPWR IF V>100 VOLTS
1237                          *        PROCEDURE
1238                          *
1239                          *        SHUTDOWN = 1
1240                          *        WAIT 20 MSEC
1241                          *        AFB=AFB/2
1242                          *        SHUTDOWN = 0
1243                          *        IF VOLD<=VNEW
1244                          *        THEN GOTO ERROR
1245                          *        ELSE
1246                          *        GOTO GETPWR
1247                          *
1248                          **************************************

1249                                   ORG     400H
1250  0400                   OVOLT4    PORT    RESET,0
1269  0409                             RECALL  AFB,0
1275  040C  97                         CLR     C              CARRY = 0 FOR SHIFT OP.
1276  040D  67                         RRC     A              AFB/2
1277  040E  96 11                      JNZ     S+3
1278  0410  17                         INC     A              MAKE SURE AFB>0
1279  0411  B8 08                      MOV     R0,#DAC
1280  0413  90                         MOVX    @R0,A          NEW DAC VOLTAGE
1281  0414                             STORE   AFB,0
1287  0417                             WAIT    20H            SETTLING TIME
1300  041D                             PORT    RESET,1          UNASSERT RESET
1319  0426                             RECALL  VSEN,1,R4
1325  042A                             ADC     VSEN           NEW V IN RA
1335  0439                             SUBTR   R4             A HAS NEWV-OLDV,CARRY IF POS.
1343  0441  E6 45                      JNC     S+4
1344  0443  44 23                      JMP     ERROR
1345  0445  24 00                      JMP     GETPWR         IF OLDV>NEWV,WE ARE OK

1347                          **************************************
1348                          *
1349                          *        OCCUR ROUTINE
1350                          *
1351                          *        CALLED FROM GETPWR IF I>1 AMP
1352                          *        PROCEDURE
1353                          *
1354                          *        SHUTDOWN = 1
1355                          *        WAIT 20 MSEC
1356                          *        AFB=AFB/2
1357                          *        SHUTDOWN = 0
1358                          *        IF IOLD<=INEW
1359                          *        THEN GOTO ERROR
1360                          *        ELSE
1361                          *        GOTO GETPWR
1362                          *
1363                          **************************************

1305  0447                   OCCUR4    PORT    RESET,0
1304  0450  23 0A                      MOV     A,#10          SET DACVOLTS TO 5 FOR RESTART
1305  0452  B8 08                      MOV     R0,#DAC
1306  0454  90                         MOVX    @R0,A          NEW DAC VOLTAGE
1307  0455                             STORE   AFB,0
1393  0458                             WAIT    60H            SETTLING TIME
1406  045E                             PORT    RESET,1          UNASSERT RESET
1425  0467                             RECALL  ISEN,1,R4
1431  046B                             ADC     ISEN           NEW I IN RA
1441  047A                             SUBTR   R4             A HAS NEWI-OLDI,CARRY IF POS.
1449  0462  E6 B0                      JNC     S+4
1450  0464  44 23                      JMP     ERROR
1451  0466  24 00                      JMP     GETPWR         IF OLDI>NEWI,WE ARE OK
                                       LIST    S
1453
1454                          **************************************
1455                          *
1456                          *        ROUTINE POWCOM
1457                          *
1458                          *        THIS ROUTINE COMPUTES CORECT AS
1459                          *
1460                          *        SQRT(PREQ/POWER)-1
1461                          *        IF CORECT>1, F1 IS SET
1462                          *        IF CORECT<1, F1 CLEARED
1463                          *
1464                          *        ROUTINE THEN GOES TO AFBADJ
1465                          *
1466                          *
1467                          **************************************

1469  0469                   POWCOM    RECALL  POWER,1,R4
1475  046C                             RECALL  PREQ,0
1481  046F  B9 04                      MOV     COUNT,#4       #F WILL DIVIDE PREQ BY 4
1482  0491  67                LOOPH    RRC     A              BY SHIFTING RIGHT TWICE
1483  0492  2A                         XCH     A,R2
1484  0493  E9 91                      DJNZ    COUNT,LOOPH
1485  0495  2A                         XCH     A,R2
1486  0496  53 C0                      ANL     A,#0C0H
1487  0498  2A                         XCH     A,R2
1488  0499  53 3F                      ANL     A,#3FH         A,R2=00XXXXXA,XX000000
1489  049B  2A                         XCH     A,R2           R2,A=00XXXXAXA,XX000000
```

```
1490  049C  74 66              CALL    DIV
1491  049F  E6 A9              JNC     ROOTER        IF CARRY, NEED LOTS POWER
1492  04A0  A5                 CLR     F1
1493  04A1  B5                 CPL     F1            F1 SET FOR UP
1494  04A2  23 FF              MOV     A,#0FFH       MAX CORECT
1495  04A4                     STORE   CORECT,0
1501  04A7  C4 00              JMP     AFBADJ
1502  04A9  74 9C    ROOTER    CALL    SQRT          GET PRED/4*POWER**1/2
1503  04AB  97                 CLR     C
1504  04AC  F7                 RLC     A             DOUBLE THE ANSWER
1505  04AD  A5                 CLR     F1            F1=0 FOR CORECT<1
1506  04AE  E6 B1              JNC     CORSET        IF CORECT<=1
1507  04B0  B5                 CPL     F1            IF CORECT>1
1508  04B1           CORSET    STORE   CORECT,0
1514  04B4  C4 00              JMP     AFBADJ 1516
1517                 ****************************
1518                 *
1519                 *      ROUTINE AFBADJ
1520                 *
1521                 *      CHECKS THE VALUE OF DWNCNT
1522                 *      IF F1 IS CLEAR (CORRECTION IS DOWN)
1523                 *      INCREMENTS DWNCNT. DWNCNT>4 MEANS ERROR
1524                 *      IF F1 SET, DWNCNT SET TO ZERO.
1525                 *
1526                 *      COMPUTES A NEW AFB BY THE FORMULA
1527                 *
1528                 *      AFB=AFB*(F1)+AFB*CORECT
1529                 *
1530                 *      WHERE CORECT IS LESS THAN ONE
1531                 *      AFB EQUALS ZERO AND AFB<ZERO ARE LOCKED OUT
1532                 *
1533                 *      IF AFB=1 AND F1 IS SET, THE NEW AFB=0.
1534                 ****************************

1535                           ORG     600H
1536  0600       AFBADJ        RECALL  POWER,0       IF POWER LESS THAN 5 WATTS(15 COUNTS)
1542  0603  03 F0              ADD     A,#0F0H       WE DONT WANT TO PANIC.
1543  0605  F6 0B              JC      TESTIT        TESTIT CHECKS FOR UP OR DOWN CORRECTION
1544  0607  B9 2E              MOV     R1,#DWNCNT    STORAGE ADDRESS FOR CLRCNT
1545  0609  C4 21              JMP     CLRCNT        SETS DWNCNT TO ZERO
1546  060B       TESTIT        RECALL  DWNCNT,0      IS #OF TIMES CORRECT IS <0
1552  060E  76 21              JF1     CLRCNT        IF CORRECTION IS UP
1553  0610  17                 INC     A             INCREMENT DWNCNT
1554  0611  A1                 MOV     @R1,A         STORE NEW DWNCNT
1555  0612  03 F6              ADD     A,#0F6H       CARRY SET IF DWNCNT>10
1556  0614  F6 1F              JC      ERCALL        IF DWNCNT>10
1557  0616  03 06              ADD     A,#06         CARRY IF DWNCNT>4
1558  0618  E6 23              JNC     OLDAFB
1559  061A                     RECALL  CORECT,0
1565  061D  F2 23              JB7     OLDAFB        IF CORECT>0.5, WAIT SOME MORE
1566  061F  A4 00  ERCALL      JMP     ERROR5        IF DWNCNT>10 OR CORECT<.5(AND)DWNCNT>3
1567  0621  27     CLRCNT      CLR     A             DWNCNT SET TO 0 IF CORRECTION UP(
1568  0622  A1                 MOV     @R1,A         STORE NEW DWNCNT AND CONTINUE
1569  0623         OLDAFB      PORT    MAXD,0        MAX DRIVE LITE OFF UNLESS
1588  062C                     RECALL  AFB,1,R4
1594  0630  96 34              JNZ     LOOPT
1595  0632  23 01              MOV     A,#1          IF WAS ZERO IS NOW ONE
1596  0634  07     LOOPT       DEC     A             IF AFB=1, A IS NOW 0
1597  0635  96 3E              JNZ     GOON          CONTINUE AS ALWAYS
1598  0637  17                 INC     A
1599  0638  17                 INC     A             A IS NOW TWO
1600  0639  76 5C              JF1     NEWANS        IF UP FLAG SET.
1601  063B  07                 DEC     A             RESTORE AFB TO ONE
1602  063C  C4 5C              JMP     NEWANS
1603  063F         GOON        RECALL  CORECT,0
1609  0641  74 50              CALL    MUL           A:R2=AFB(CORECT)
1610  0643  2A                 XCH     A,R2
1611  0644                     ROUND   R2
1616  0648  B5                 CPL     F1
1617  0649  76 59              JF1     DOWN
1618  064B  6C                 ADD     A,R4          IF F1 WAS SET, ADD AFB TO AFB*CORECT
1619  064C  E6 59              JNC     DOWN
1620  064E                     PORT    MAXD,1        MAXIMUM DRIVE LITE
1639  0657  23 FF              MOV     A,#255        IF CARRY,AFB>256 SO SET AFB=255
1640  0659  96 5C  DOWN        JNZ     NEWANS
1641  065B  17                 INC     A             IF WAS ZERO IS NOW ONE
1642  065C         NEWANS      STORE   AFB,0
1648  065F  B9 0B              MOV     R1,#DAC
1649  0661  91                 MOVX    @R1,A
1650  0662                     WCHDOG
1679  0672                     RECALL  MODES,1,R4    THIS IS LAST MODE NUMBERS
1685  0676  0A                 IN      A,P2          GET NEW KEYING SIGNALS
1686  0677  53 70              ANL     A,#70H        DSE,DS1E,DS2E
1687  0679  37                 CPL     A
1688  067A  6C                 ADD     A,R4
1689  067B  37                 CPL     A             ZERO IF NO CHANGE
1690  067C  C6 80              JZ      WARMUP        IF NO CHANGE
1691  067E  04 00              JMP     INIT
1692  0680  24 00  WARMUP      JMP     GETPWR        AND CONTINUE
1693                 ****************************
1694                 *
1695                 *      KILL ROUTINE
1696                 *      SETS KEY OFF
1697                 *              SHUTDOWN ON
1698                 *              RESET ON
1699                 *              AFB TO ZERO
1700                 *
1701                 *      BRANCH AND HANG
1702                 *
1703                 ****************************
```

```
1705  0682                KILL6    PORT     KEY,1
1724  068B                         PORT     RESET,0
1743  0694                         WAIT     5
1756  069A                         PORT     RESET,0     DUMMY INSTR. TO REMOVE SDN INST.
1775  06A3  27                     .CLR     A
1776  06A4  B9 08                  MOV      R1,#DAC
1777  06A6                         STORE    AFB,0
1783  06A9  91                     MOVX     @R1,A       SET DAC VOLTS TO ZERO
1784  06AA                         PORT     ERLITE,1    TURN ON ERROR LED
1803  06B3  C4 82                  JMP      KILL6       BRANCH AND HANG

1805                     ****************************
1806                     *
1807                     *        ERROR ROUTINE
1808                     *
1809                     *        THIS ROUTINE CHECKS THE CONDITION
1810                     *        OF THE DC SWITCHER TO DETERMINE IF
1811                     *        THE OUTPUT POWER IS CONTROLLABLE.
1812                     *        EXITS TO COLDST IF STILL OK,
1813                     *        TO KILL OTHERWISE.
1814                     *
1815                     ****************************

1816                              ORG      500H
1917  0500                ERROR5   PORT     KEY,1       KEY OFF
1836  0509                         WCHDOG
1865  0519                         PORT     RESET,1
1884  0522                         PORT     ERLITE,1
1903  052B                         ADC      DCSEN       DCVOLTAGE AT RPLUS
1913  053A  AE                     MOV      R6,A        TEMP STORAGE FOR OLD DCSEN
1914  053B  B9 08                  MOV      R1,#DAC
1915  053D  27                     CLR      A
1916  053E  91                     MOVX     @R1,A       AFB EQUALS ZERO
1917  053F  FE            DC50     MOV      A,R6        DCSEN
1918  0540  03 9B                  ADD      A,#155
1919  0542  F6 4D                  JC       DCCHK       CARRY IF VOLTS>50
1920  0544  A4 A1                  JMP      COOLDN      IF VOLTS LOW.
1921  0546  BF 0A         DCCHK    MOV      R7,#10      COUNTER REG.
1922  0548                         ADC      DCSEN
1932  0557  AD                     MOV      R5,A        R5 IS NEWVOLTS
1933  0558  37                     CPL      A
1934  0559  6E                     ADD      A,R6        A=OLD-NEW
1935  055A  F6 7B                  JC       RESETCK     CARRY IF OLD>NEW
1936  055C  FD                     MOV      A,R5
1937  055D  AE                     MOV      R6,A        OLDVOLTS UPDATE
1938  055E                         WAIT     10
1951  0564                         WCHDOG
1960  0574  EF 4D                  DJNZ     R7,DCCHK    REPEAT 10 TIMES
1961  0576  A4 9B                  JMP      KILL5       IF NO IMPROVEMENT
1962  0578          RESETCK        PORT     RESET,1     RESET OFF
2001  0581                         WAIT     100
2014  058F                         ADC      DCSEN
2024  0596  AD                     MOV      R5,A
2025  0597  37                     CPL      A
2026  0598  6E                     ADD      A,R6        OLD-NEW, CARRY IF POSITIVE
2027  0599  F6 A1                  JC       COOLDN      IF NO INCREASE
2028  059B  03 F5                  ADD      A,#245      MINUS 10
2029  059D  F6 A1                  JC       COOLDN      IF SMALL INCREASE
2030  059F  A4 9B                  JMP      KILL5       OTHERWISE
2031  05A1  BF 64         COOLDN   MOV      R7,#100     COUNTER REG.
2032  05A3           COOL1         WCHDOG
2061  05B3                         ADC      DCSEN
2071  05C2  03 C8                  ADD      A,#200
2072  05C4  E6 D0                  JNC      COOL2       IF VOLTS.LT.20
2073  05C6                         WAIT     100
2086  05CC  EF A3                  DJNZ     R7,COOL1    LOOP 100 TIMES
2087  05CE  A4 9B                  JMP      KILL5
2088  05D0          COOL2          PORT     ERLITE,0
2107  05D9  04 65                  JMP      COLDST      RESTART IF SWITCHER OK
2108  05DB  C4 82         KILL5    JMP      KILL6       PAGING PROBLEMS.

2111                     ****************************
2112                     *
2113                     *        TEST LOOP
2114                     *
2115                     *        THIS PROGRAM WAITS 5 SECONDS TO KILL
2116                     *        THE WATCHDOG TIMER
2117                     *        THEN READS ONE OF FOUR ADC CHANNELS
2118                     *        AND DUMPS IT TO THE DAC
2119                     *        REPEATS FOR EACH CHANNEL FOREVER
2120                     *
2121                     ****************************
2122                              ORG      0700H
2123  0700                TESTLP   PORT     KEY,1
2142  0709                         PORT     RESET,0
2161  0712                         PORT     SDN,0
2180  071B  BD 20                  MOV      R5,#20H
2181  071D                LOOP10   WAIT     255
2194  0723  ED 1D                  DJNZ     R5,LOOP10   WAIT 2000H CYCLES.
2195  0725  B8 08                  MOV      R0,#08      DAC ADDRESS
2196  0727  F9            LOOPV    MOV      A,R1        ADC CHANNEL
2197  0728  17                     INC      A
2198  0729  53 03                  ANL      A,#3        CHANNEL = 0 1 2 OR 3
2199  072B  A9                     MOV      R1,A
2200  072C  BC 00                  MOV      R4,#00
2201  072E  EB 34         ICNT     DJNZ     R3,LOOPU
2202  0730  1C                     INC      R4          HI BYTE OF LOOP COUNTER
2203  0731  FC                     MOV      A,R4
2204  0732  72 27                  JB3      LOOPV       IF COUNTER=8*255
2205  0734  91            LOOPU    MOVX     @R1,A       ADC CONVERSION
2206  0735  BD 08                  MOV      R5,#8       WAIT FOR EOC TO DROP
```

```
2207  0737  ED 37         LOOPW    DJNZ    R5,LOOPW
2208  0739  B6 3D                  JNI     LOOPX        IF EOC DOWN
2209  073B  E4 39                  JMP     $-2
2210  073D  81            LOOPX    MOVX    A,@R1        GET ADC VALUE
2211  073E  90                     MOVX    @R0,A        DUMP IT TO DAC
2212  073F  0A                     IN      A,P2
2213  0740  43 BF                  ORL     A,#BFH
2214  0742  37                     CPL     A            ZERO IF DSE,DS1E AND DS2E
2215  0743  C6 2E                  JZ      ICNT
2216  0745  04 00                  JMP     INIT
2217  0747  E4 2E                  JMP     ICNT         LOOP THROUGH AGAIN
2218  0749                  END
```

SYMBOL TABLE

| Name | Addr | Name | Addr | Name | Addr | Name | Addr |
|---|---|---|---|---|---|---|---|
| AF6 | 0028 | AF6ADJ | 0600 | CKI | 0164 | CKV | 0129 |
| CKVMX | 0132 | CLUZ | 0227 | CLRCNT | 0621 | CMIDZ | 0233 |
| CNTLP | 0200 | COLDST | 0065 | COOL1 | 05A3 | COOL2 | 0500 |
| COULDN | 05A1 | CORECT | 0029 | CORGET | 0278 | CORSET | 04B1 |
| DAC | 0008 | DC50 | 053F | DCCHK | 0546 | DCSEN | 0023 |
| DIV | 0366 | DIVIA | 0371 | DIVIB | 038A | DIVIC | 0386 |
| DIVID | 0367 | DIVIE | 037E | DIVILP | 0372 | DOG | 0008 |
| DOWN | 0659 | DWNCNT | 002E | ECON | 0020 | ENDINT | 0063 |
| ERCALL | 061F | ERLITE | 0080 | ERROR | 0223 | ERROR5 | 0500 |
| GETI | 013E | GETPWR | 0100 | GOON | 063E | HIZR2 | 023A |
| HOUSE | 016D | HOUSE1 | 0179 | ICNT | 072E | IFL | 015B |
| IFLAG | 0010 | IMAX | 0028 | INIT | 0000 | ISEN | 0022 |
| KEY | 0001 | KILL5 | 05DB | KILL6 | 0682 | LOOP1 | 017D |
| LOOP10 | 0710 | LOOP2 | 020D | LOOP6 | 0045 | LOOP8 | 0061 |
| LOOPE | 03A5 | LOOPF | 03A2 | LOOPH | 0491 | LOOPS | 0240 |
| LOOPT | 0634 | LOOPU | 0734 | LOOPV | 0727 | LOOPW | 0737 |
| LOOPX | 073D | LOOPZ | 016E | LOZ | 01A2 | MAXD | 0040 |
| MIDZ | 0198 | MODES | 002F | MPY8A | 035E | MPY8LP | 0354 |
| MUL | 0350 | NEWANS | 065C | NEWSET | 0274 | OCCUR | 0221 |
| OCCUR4 | 0447 | ULDAFB | 0623 | OVOLT | 021F | OVOLT4 | 0400 |
| P1MAGE | 002D | POWCOM | 0488 | POWER | 0026 | PREO | 0027 |
| R220L | 0268 | RA1 | 0096 | RA2 | 0095 | RAMCHK | 0034 |
| RESET | 0002 | RESETC | 0578 | ROM | 005B | ROM1 | 01F4 |
| ROM2 | 02F0 | ROM3 | 03F4 | ROM4 | 04F0 | ROM5 | 05F0 |
| ROM6 | 06F0 | ROM7 | 07F0 | ROMST | 00F0 | ROOTER | 04A9 |
| RTECON | 002A | SDN | 0004 | SORT | 038C | TESTIT | 060B |
| TESTLP | 0700 | TMP | 00AA | TST | 0093 | VFL | 0120 |
| VFLAG | 0020 | VMAX | 0217 | VMAX2 | 021B | VMAXR1 | 002B |
| VMAXR2 | 002C | VSEN | 0021 | WARMUP | 0680 | Z | 0024 |
| ZOL | 0225 | ZOL2 | 0258 | ZRANGE | 0025 | ZRSTO | 01A6 |

We claim:

1. An electrosurgical generator comprising a source of electrosurgical energy;
   means adapted for connecting said source to a patient;
   means for measuring the impedance of the patient; and
   control means responsive to said patient impedance measuring means for decreasing the output power from said source with increasing patient impedance, the rate of power decrease being substantially greater than that which would result if the output voltage from the source were maintained constant over the range of increasing patient impedance and substantially less than that which would result if the source of electrosurgical energy were disabled.

2. A generator as in claim 1 where said control means includes means for decreasing the output power over the range of increasing patient impedance in accordance with the inverse of the square of said impedance.

3. An electrosurgical generator comprising an adjustable source of a electrosurgical energy;
   means adapted for connecting said source to a load including a patient; and
   control means for adjusting the actual power delivered to said load from said source including;
   means for determining the impedance of said load;
   means responsive to all said impedance above a first predetermined value for computing a correction factor depending on the value of said impedance, said correction factor corresponding to a required load power, said correction factor computing means including means for computing the correction factor so that the power delivered to said load is decreased with increasing patient impedance, the rate of power decrease being substantially greater than that which would result if the output voltage from said source were maintained constant over the range of increasing patient impedance and substantially less than that which would result if said source were disabled; and
   means responsive to said correction factor for adjusting said source of electrosurgical power so that said actual power follows said required power.

4. A generator as in claim 3 where said control means includes a microprocessor for adjusting the actual power delivered to said load from said source.

5. A generator as in claim 3 including means for selecting a nominal power to be delivered to said load where said correction factor also depends on the nominal power to compute the correction factor.

6. A generator as in claim 5 where said means for selecting a nominal power includes means for extending the nominal power from 0–70 watts.

7. A generator as in claim 3 including a heat sink for said source of electrosurgical energy, the heat sink having a capacity of not more than about 4 watts.

8. A generator as in claim 3 where, for all load impedances less than a second lower predetermined value, said correction factor computing means includes means for computing the correction factor so that the current through said load remains substantially constant.

9. A generator as in claim 8 including means for selecting a nominal power to be delivered to said load and where said correction factor computing means includes means for computing the correction factor as $I_{MAX}/I_{SEN}$ where $I_{MAX}$ is the current through an impedance of said second predetermined value having said nominal power applied thereto and $I_{SEN}$ is the actual current through said load.

10. A generator as in claim 8 including means for setting said second predetermined value to about 70 ohms.

11. A generator as in claim 3 where for all load impedances between said first predetermined value first and a second lower predetermined value, said correction factor computing means includes means for computing the correction factor so that the power delivered to said load remains substantially constant.

12. A generator as in claim 11 including means for selecting a nominal power to be delivered to said load and where said correction factor computing means includes means for computing the correction factor as $(P_{MAX}/P_{LOAD})^{1/2}$ where $P_{MAX}$ is the nominal power and $P_{LOAD}$ is the actual power delivered to said load.

13. A generator as in claim 11 including means for setting said first and second predetermined values respectively to about 70 and 100 ohms.

14. A generator as in claim 3 where for all impedances greater than said first predetermined value, said correction factor computing means includes means for computing the correction factor so that the power delivered to said load is proportional to the inverse of the square of the load impedance.

15. A generator as in claim 14 including means for selecting a nominal power to be delivered to said load and where said correction factor computing means includes means for computing the correction factor as $[(10,000\ P_{MAX}/Z^2_{LOAD})P_{LOAD}]^{1/2}$ where $P_{MAX}$ is the nominal power, $Z_{LOAD}$ in the local impedance, and $P_{LOAD}$ is the actual power delivered to the load.

16. A generator as in claim 15 including means for setting said first predetermined value to about 100 ohms.

17. An electrosurgical generator comprising an adjustable source of electrosurgical energy;
   means adapted for connecting said source to a load including a patient; and
   control means for adjusting the power delivered to said load from said source including;
   means for measuring the impedance of the patient;
   means responsive to said patient impedance measuring means for selecting first and second modes of operation of said generator when said load impedance exceeds a predetermined value;
   means for maintaining the voltage across said load substantially constant for all values of load impedance in excess of said predetermined value in response to said first mode being selected; and
   means for reducing the power delivered to said load in accordance with the inverse of the square of the load impedance for all values of load impedance in excess of said predetermined value in response to said second mode being selected.

18. A generator as in claim 17 where said control means includes a microprocessor for adjusting the actual power to said load from said source.

19. A generator as in claim 17 wherein said means for adjusting the power delivered to said load includes means for computing a correction factor which is a function of the impedance of said load and the selected mode of operation; and
   means responsive to the correction factor for adjusting said source of electrosurgical energy so that either said first or second mode of operation is implemented depending on the selected mode.

20. A generator as in claim 19 including means for selecting a nominal power to be delivered to said load and where said correction factor computing means includes means for computing the correction factor for said first mode of operation as $V_{MAX}/V_{SEN}$ where $V_{MAX}$ is the voltage across an impedance of said predetermined value having said nominal power applied thereto and $V_{SEN}$ is the actual voltage across said load and where the correction factor for computing the correction factor for said second mode of operation is $[(10,000\ P_{MAX}/Z^2_{LOAD})P_{LOAD}]^{1/2}$ where $P_{MAX}$ is the nominal power, $Z_{LOAD}$ is the load impedance, and $P_{LOAD}$ is the actual power delivered to the load.

21. A generator as in claim 17 including means for setting said predetermined value to about 100 ohms.

* * * * *